United States Patent
Su et al.

(10) Patent No.: US 10,473,517 B2
(45) Date of Patent: *Nov. 12, 2019

(54) ACOUSTIC EMISSION SOURCE EXPANSION APPARATUS INTEGRATED HYDRAULIC ENGINEERING CONSTRUCTION BEHAVIOR FIBER SENSING DEVICE

(71) Applicant: Hohai University, Nanjing, Jiangsu (CN)

(72) Inventors: Huaizhi Su, Jiangsu (CN); Meng Yang, Jiangsu (CN); Chongshi Gu, Jiangsu (CN); Hezhi Liu, Jiangsu (CN); Hong Luo, Jiangsu (CN)

(73) Assignee: Hohai University, Nanjing, Jiangsu (CN)

( * ) Notice: Subject to any disclaimer, the term of this patent is extended or adjusted under 35 U.S.C. 154(b) by 110 days.

This patent is subject to a terminal disclaimer.

(21) Appl. No.: 15/834,410

(22) Filed: Dec. 7, 2017

(65) Prior Publication Data

US 2019/0178707 A1 Jun. 13, 2019

(51) Int. Cl.
   *G01H 9/00* (2006.01)
   *G02B 6/44* (2006.01)
   *G01N 29/14* (2006.01)

(52) U.S. Cl.
   CPC ............ *G01H 9/004* (2013.01); *G01N 29/14* (2013.01); *G02B 6/4471* (2013.01)

(58) Field of Classification Search
   CPC .... G01N 29/2462; G01N 29/28; G01N 29/14; G01N 29/2406; G01N 29/11; G01N 29/2418; G01H 9/004
   See application file for complete search history.

(56) References Cited

U.S. PATENT DOCUMENTS

| | | | | |
|---|---|---|---|---|
| 4,487,068 A | * | 12/1984 | Hawkins | G01N 29/14 73/159 |
| 5,381,695 A | * | 1/1995 | Payne | B23D 79/023 73/643 |
| 5,656,428 A | * | 8/1997 | McAllister | G01N 33/54373 204/193 |
| 5,804,725 A | * | 9/1998 | Posakony | G01N 29/2462 73/590 |
| 2011/0288689 A1 | * | 11/2011 | Kageyama | A01G 7/00 700/284 |
| 2012/0103098 A1 | * | 5/2012 | Laugharn, Jr. | B01F 11/0283 73/644 |

* cited by examiner

*Primary Examiner* — Helen C Kwok
(74) *Attorney, Agent, or Firm* — Rankin, Hill & Clark LLP

(57) ABSTRACT

An acoustic emission source expansion apparatus integrated hydraulic engineering construction behavior fiber sensing device includes a base plate, a first side plate and a second side plate fixedly connected with two sides of the base plate, the top portion of the first side plate is connected with the top portion of the second side plate through an arc-shaped fiber-carrying channel, and a main common cavity is formed by the base plate, the first side plate, the second side plate and the arc-shaped fiber-carrying channel; a pair of sensing fibers is arranged in the arc-shaped fiber-carrying channel, the sensing fibers are tightly pressed in the arc-shaped fiber-carrying channel through a pressing block, the pressing block is provided with a plurality of springs, the springs tightly press the pressing block through a cover plate, and the cover plate is arranged on the first side plate and the second side plate.

6 Claims, 1 Drawing Sheet

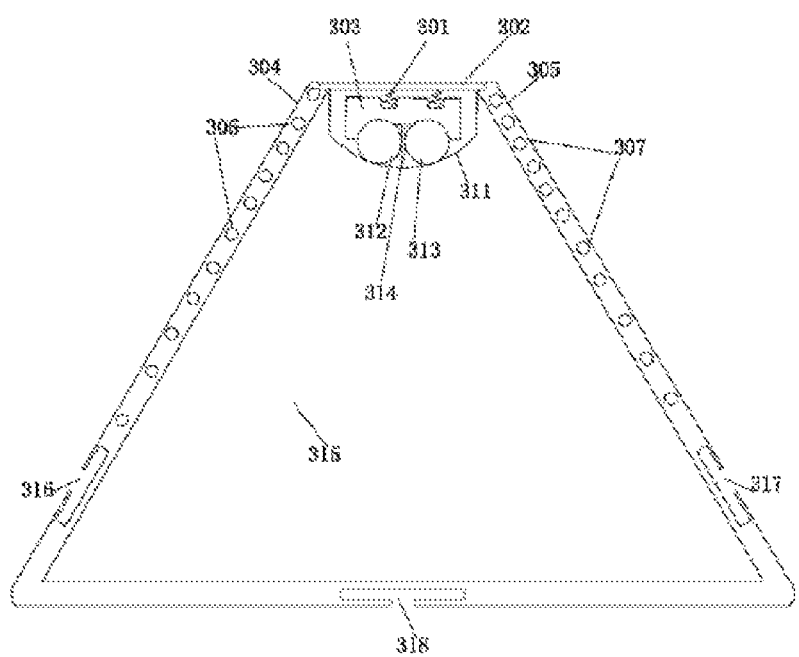

ACOUSTIC EMISSION SOURCE EXPANSION APPARATUS INTEGRATED HYDRAULIC ENGINEERING CONSTRUCTION BEHAVIOR FIBER SENSING DEVICE

TECHNICAL FIELD

The present invention relates to an acoustic emission source expansion apparatus integrated hydraulic engineering construction behavior fiber sensing device, and belongs to the field of hydraulic structure health monitoring.

BACKGROUND

A sensing fiber has two functions of "transmitting" and "sensing" at the same time. There are a variety of sensors based on a fiber sensing technology. The same parameter may be measured by different types of sensors, but the core idea of the fiber sensing technology is to detect the modulation of light by external parameters. The sensing fibers are divided into an intensity modulation type, a phase modulation type, a frequency modulation type, a wavelength modulation type, a polarization state modulation type, and other types according to the modulated theory of the light in the fiber. With the development of light information and sensing technology, the fiber sensing technology has been greatly improved, and has the advantages on sensing manner, sensing principle, signal detection and processing, and other aspects that the traditional electric sensor does not have.

The acoustic emission technology is an advanced non-destructive testing technology, which finds out the damage, fracture, deformation and other information in a tested object through detecting and analyzing an acoustic wave sent by the tested object itself. The technology is widely used in petroleum, aviation, construction and other fields. A key component of acoustic emission is an acoustic emission sensor for collecting and detecting the acoustic wave. The traditional acoustic emission sensor manufactured through piezoelectric ceramics or piezoelectric crystal materials has the defects of poor anti-electromagnetic interference capability and short signal transmission, and the defects of poor anti-electromagnetic interference capability and short signal transmission can be prevented through integrating the fiber sensing technology with the acoustic emission technology. Moreover, the fiber sensing technology can remedy the capability of the acoustic emission that the temperature and other information cannot be monitored. Therefore, integrating the fiber sensing technology with the acoustic emission sensing technology will greatly extend the sensing monitoring and detection capabilities of a structure, but how to collect and enhance the acoustic wave in the acoustic emission technology preferably and how to arrange the sensing fibers preferably have not been reported yet in the current field of integrating the fiber sensing technology with acoustic emission technology.

SUMMARY

Object of the Invention

In order to overcome the defects in the prior art, the present invention provides an acoustic emission source expansion apparatus integrated hydraulic engineering construction behavior fiber sensing device, which constructs a multi-level multi-different duration acoustic emission source by being provided with a plurality of first through holes, second through holes and the main common cavity and increasing the transmission of the acoustic wave, so as to realize influences on light information in the sensing fiber at multi-levels and multi-different durations.

Technical Solution

In order to solve the technical problems above, the present invention provides an acoustic emission source expansion apparatus integrated hydraulic engineering construction behavior fiber sensing device, which comprises a base plate, and a first side plate and a second side plate fixedly connected with two sides of the base plate, wherein the top portion of the first side plate is connected with the top portion of the second side plate through an arc-shaped fiber-carrying channel, and a main common cavity is formed by the base plate, the first side plate, the second side plate and the arc-shaped fiber-carrying channel; and a pair of sensing fibers is arranged in the arc-shaped fiber-carrying channel, the sensing fibers are tightly pressed in the arc-shaped fiber-carrying channel through a pressing block, the pressing block is provided with a plurality of springs, the springs tightly press the pressing block through a cover plate, and the cover plate is arranged on the first side plate and the second side plate.

Preferably, a plurality of first through holes are arranged on the first side plate along the axis direction of the sensing fiber.

Preferably, a plurality of second through holes are arranged on the second side plate along the axis direction of the sensing fiber.

Preferably, the first through hole is a common cavity circular hole, the section of the common cavity circular hole is a circular hole, the second through hole is a common cavity hexagonal hole, the section of the common cavity hexagonal hole is a hexagonal hole, and both the first through hole and the second through hole are in an odd number.

Preferably, the external surfaces of the base plate, the first side plate and the second side plate are all provided with an external groove.

Preferably, a fiber separation wall for separating two sensing fibers is arranged bellow the pressing block.

Beneficial Effects according to the acoustic emission source expansion apparatus integrated hydraulic engineering construction behavior fiber sensing device of the invention, an apparatus integrating the main common cavity, common cavity hexagonal holes and common cavity circular holes for laying a sensing fiber acoustic emission sending apparatus is firstly proposed, which innovatively constructs a multi-level multi-different duration acoustic emission source by means of multiform cavity holes, large and small-sized cavity holes and cavity holes in different spatial positions, increases the transfer of the acoustic wave, realizes influences on light information in the sensing fiber at multi-levels and multi-different durations, and provides important guarantee to monitor the service behavior of the structure preferably. The apparatus has the advantages of simple operation, low monitoring cost, complete structure, and strong processing and automation, which has significant meaning to the application and promotion of the fiber sensing and acoustic emission integrating technology in actual engineering.

BRIEF DESCRIPTION OF THE DRAWINGS

FIG. 1 is a structure diagram of the present invention.

DETAILED DESCRIPTION

An acoustic emission source expansion apparatus integrated hydraulic engineering construction behavior fiber sensing device according to the present invention comprises a base plate, and a first side plate 304 and a second side plate 305 fixedly connected with two sides of the base plate, wherein the top portion of the first side plate 304 is connected with the top portion of the second side plate 305 through an arc-shaped fiber-carrying channel 311, and a main common cavity 315 is formed by the base plate, the first side plate 304, the second side plate 305 and the arc-shaped fiber-carrying channel 311; and a pair of sensing fibers is arranged in the arc-shaped fiber-carrying channel 311, the sensing fibers are tightly pressed in the arc-shaped fiber-carrying channel 311 through a pressing block 303, the pressing block 303 is provided with a plurality of springs 301, the springs 301 tightly press the pressing block 303 through a cover plate 302, and the cover plate 302 is arranged on the first side plate 304 and the second side plate 305.

In the present invention, a plurality of first through holes 306 are arranged on the first side plate 304 along the axis direction of the sensing fiber, and a plurality of second through holes 307 are arranged on the second side plate 305 along the axis direction of the sensing fiber. The first through hole 306 is a common cavity circular hole, the section of the common cavity circular hole is a circular hole, the second through hole 307 is a common cavity hexagonal hole, the section of the common cavity hexagonal hole is a hexagonal hole, and both the first through hole 306 and the second through hole 307 are in an odd number. The external surfaces of the base plate, the first side plate 304 and the second side plate 305 are all provided with an external groove. A fiber separation wall 314 for separating two sensing fibers is arranged bellow the pressing block 303, and the fiber separation wall 314 is a VIP plate.

A running method of the acoustic emission source expansion apparatus integrated hydraulic engineering construction behavior fiber sensing device as mentioned above comprises the following steps.

(1) Determine the Number of the Apparatus Used and the Length of the Distributed Sensing Fiber A 150 m×100 m region with a perimeter of 500 m in some upstream face of some concrete dam during a construction process in the northwest is selected in the embodiment. In view of considering possible bending and a line leading purpose, it is finally determined that the length of a GJJV tight-buffered sensing fiber is 600 m. Based on the 2 m thickness of the used acoustic emission source expansion apparatus integrated hydraulic engineering construction behavior fiber sensing device and the scope of the part needing to be emphasically monitored during actual engineering, it is finally determined that 50 acoustic emission source expansion apparatus integrated hydraulic engineering construction behavior fiber sensing devices are selected, and a rubber tube is arranged in each acoustic emission source expansion apparatus integrated hydraulic engineering construction behavior fiber sensing device for embedding protection. In order to better describe the running details of the apparatus, one of the apparatuses is preferably selected for detailed discussion.

(2) Assemble a First Laying Module and a Second Laying Module

The first side plate 304 with a length of 20 cm and a width of 5 cm and the second side plate 305 with a length of 20 cm and a width of 5 cm are installed and laid at a 60-degree included angle with a horizontal plane to form the main common cavity 315, and 11 common cavity circular holes with a diameter of 3 cm and a circular section on the first side plate 304 and 11 common cavity hexagonal holes with hexagonal section and a side length of 1 cm on the second side plate 305 are checked whether to be blocked, if the holes are blocked or impassable, the holes shall be dredged, and a first sensing fiber 312 and a second sensing fiber 313 are placed in the arc-shaped fiber-carrying channel 311.

(3) Close the Apparatus, and Debug for Initial Running

The first GJJV tight-buffered sensing fiber 312 and the second GJJV tight-buffered sensing fiber 313 are fixed in a non-rigid manner through the pressing block 303, the combination form of triangle laying may better transmit the information to the first sensing fiber 312 and the second sensing fiber 313 when the acoustic emission source resonates with the common cavity circular hole, the common cavity hexagonal hole and the main common cavity 315, the first sensing fiber 312 and the second sensing fiber 313 are connected to an instrument to be monitored for initial debugging, and the running condition of the apparatus is checked;

(4) Embed the Apparatus to Finish Laying

A part capable of being fixed in the structure to be monitored is selected, which depends on a steel bar structure in the embodiment. Therefore, a first external groove with an opening having a height of 2 cm and a width of 4 cm, a second external groove with an opening having a height of 2 cm and a width of 4 cm, and a bottom external groove with an opening having a height of 1 cm and a width of 5 cm are respectively passed through a steel bar component in the structure to be monitored, and the apparatuses are laid and installed in sequence according to the order from near to far, from straight to bent, and from top to bottom. After all the apparatuses are completely laid, the apparatuses are embedded to finish the final laying.

The description above is only the preferable embodiment of the present invention, and it should be noted that those skilled in the art may make a plurality of improvements and decorations without departing from the principle of the present invention, and these improvements and decorations shall also fall within the protection scope of the present invention.

The invention claimed is:

1. An acoustic emission source expansion apparatus integrated hydraulic engineering construction behavior fiber sensing device, comprising a base plate, and a first side plate and a second side plate fixedly connected with two sides of the base plate, wherein a top portion of the first side plate is connected with a top portion of the second side plate through an arc-shaped fiber-carrying channel, and a main common cavity is formed by the base plate, the first side plate, the second side plate and the arc-shaped fiber-carrying channel; and a pair of sensing fibers is arranged in the arc-shaped fiber-carrying channel, the sensing fibers are tightly pressed in the arc-shaped fiber-carrying channel through a pressing block, the pressing block is provided with a plurality of springs, the springs tightly press the pressing block through a cover plate, and the cover plate is arranged on the first side plate and the second side plate.

2. The acoustic emission source expansion apparatus integrated hydraulic engineering construction behavior fiber sensing device according to claim 1, wherein a plurality of first through holes are arranged on the first side plate along an axis direction of the sensing fiber.

3. The acoustic emission source expansion apparatus integrated hydraulic engineering construction behavior fiber sensing device according to claim 2, wherein a plurality of second through holes are arranged on the second side plate along the axis direction of the sensing fiber.

4. The acoustic emission source expansion apparatus integrated hydraulic engineering construction behavior fiber sensing device according to claim 3, wherein the first through hole is a common cavity circular hole, a section of the common cavity circular hole is a circular hole, the second through hole is a common cavity hexagonal hole, a section of the common cavity hexagonal hole is a hexagonal hole, and both the first through hole and the second through hole are in an odd number.

5. The acoustic emission source expansion apparatus integrated hydraulic engineering construction behavior fiber sensing device according to claim 1, wherein the external surfaces of the base plate, the first side plate and the second side plate are all provided with an external groove.

6. The acoustic emission source expansion apparatus integrated hydraulic engineering construction behavior fiber sensing device according to claim 1, wherein a fiber separation wall for separating two sensing fibers is arranged below the pressing block.

\* \* \* \* \*